US010502694B2

(12) United States Patent
Dziura et al.

(10) Patent No.: US 10,502,694 B2
(45) Date of Patent: Dec. 10, 2019

(54) METHODS AND APPARATUS FOR PATTERNED WAFER CHARACTERIZATION

(71) Applicant: KLA-Tencor Corporation, Milpitas, CA (US)

(72) Inventors: Thaddeus Gerard Dziura, San Jose, CA (US); Stilian Ivanov Pandev, Santa Clara, CA (US); Alexander Kuznetsov, Mountain View, CA (US); Andrei V. Shchegrov, Campbell, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 1022 days.

(21) Appl. No.: 14/449,646

(22) Filed: Aug. 1, 2014

(65) Prior Publication Data
US 2015/0046121 A1  Feb. 12, 2015

Related U.S. Application Data

(60) Provisional application No. 61/862,801, filed on Aug. 6, 2013, provisional application No. 61/943,098, filed on Feb. 21, 2014.

(51) Int. Cl.
G01N 21/956 (2006.01)
G01N 21/95 (2006.01)

(52) U.S. Cl.
CPC ....... *G01N 21/956* (2013.01); *G01N 21/9501* (2013.01); *G01N 2201/12* (2013.01)

(58) Field of Classification Search
CPC ............. G01N 21/956; G01N 21/9501; G01N 2201/12

USPC ........................................................ 702/179
See application file for complete search history.

(56) References Cited

U.S. PATENT DOCUMENTS

| 7,289,219 | B2 | 10/2007 | Norton et al. |
| 7,414,733 | B2 | 8/2008 | Bischoff et al. |
| 7,417,750 | B2 | 8/2008 | Vuong et al. |
| 7,463,369 | B2 | 12/2008 | Wack et al. |
| 7,990,549 | B2 | 8/2011 | Walsh |
| 2003/0219153 | A1 | 11/2003 | Levin et al. |
| 2004/0080761 | A1 | 4/2004 | Du-Nour et al. |

(Continued)

FOREIGN PATENT DOCUMENTS

| CN | 1732372 A | 2/2006 |
| CN | 101707180 A | 5/2010 |

(Continued)

OTHER PUBLICATIONS

"International Application Serial No. PCT/US2014/049743, Search Report and Written Opinion dated Nov. 28, 2014", 12 pgs.

(Continued)

Primary Examiner — Ricky Ngon
(74) Attorney, Agent, or Firm — Kwan & Olynick LLP

(57) ABSTRACT

Disclosed are apparatus and methods for characterizing a plurality of structures of interest on a semiconductor wafer. A plurality of spectra signals are measured from a particular structure of interest at a plurality of azimuth angles from one or more sensors of a metrology system. A difference spectrum is determined based on the spectra signals obtained for the azimuth angles. A quality indication of the particular structure of interest is determined and reported based on analyzing the difference spectrum.

27 Claims, 10 Drawing Sheets

(56) References Cited

U.S. PATENT DOCUMENTS

| | | | |
|---|---|---|---|
| 2005/0088665 A1* | 4/2005 | Bischoff | G01N 21/956 356/601 |
| 2005/0174575 A1 | 8/2005 | Norton et al. | |
| 2008/0018874 A1 | 1/2008 | Dusa et al. | |
| 2008/0206993 A1 | 8/2008 | Lee et al. | |
| 2009/0059236 A1* | 3/2009 | Meeks | G01B 11/065 356/445 |
| 2009/0073448 A1* | 3/2009 | Tenner | G01N 21/55 356/446 |
| 2009/0076999 A1* | 3/2009 | De Mol | G03F 7/705 706/52 |
| 2009/0296090 A1* | 12/2009 | Saha | G01N 21/9501 356/369 |
| 2010/0114522 A1* | 5/2010 | Chung | G03F 9/7003 702/150 |
| 2011/0128512 A1* | 6/2011 | Pellemans | G03F 7/70633 355/27 |
| 2011/0141272 A1* | 6/2011 | Uto | G01N 21/9501 348/135 |
| 2012/0287435 A1* | 11/2012 | Adams | G01N 21/51 356/340 |
| 2013/0148116 A1* | 6/2013 | Tanaka | G01N 21/95623 356/237.5 |
| 2013/0151440 A1* | 6/2013 | Li | G01N 21/956 706/12 |
| 2015/0001087 A1* | 1/2015 | Dinneen | H01L 21/67253 205/81 |

FOREIGN PATENT DOCUMENTS

| | | |
|---|---|---|
| JP | 2006504092 A | 2/2006 |
| TW | 200849416 A | 12/2008 |

OTHER PUBLICATIONS

TW Office Action and Search Report, dated Jan. 17, 2018, Applicant KLA-Tencor Corp., Application No. TW103126977, Filed Aug. 6, 2014, 12 pages.

Chinese Office Action and English Translation for Application No. 201480054194.1 dated Jan. 26, 2018.

* cited by examiner

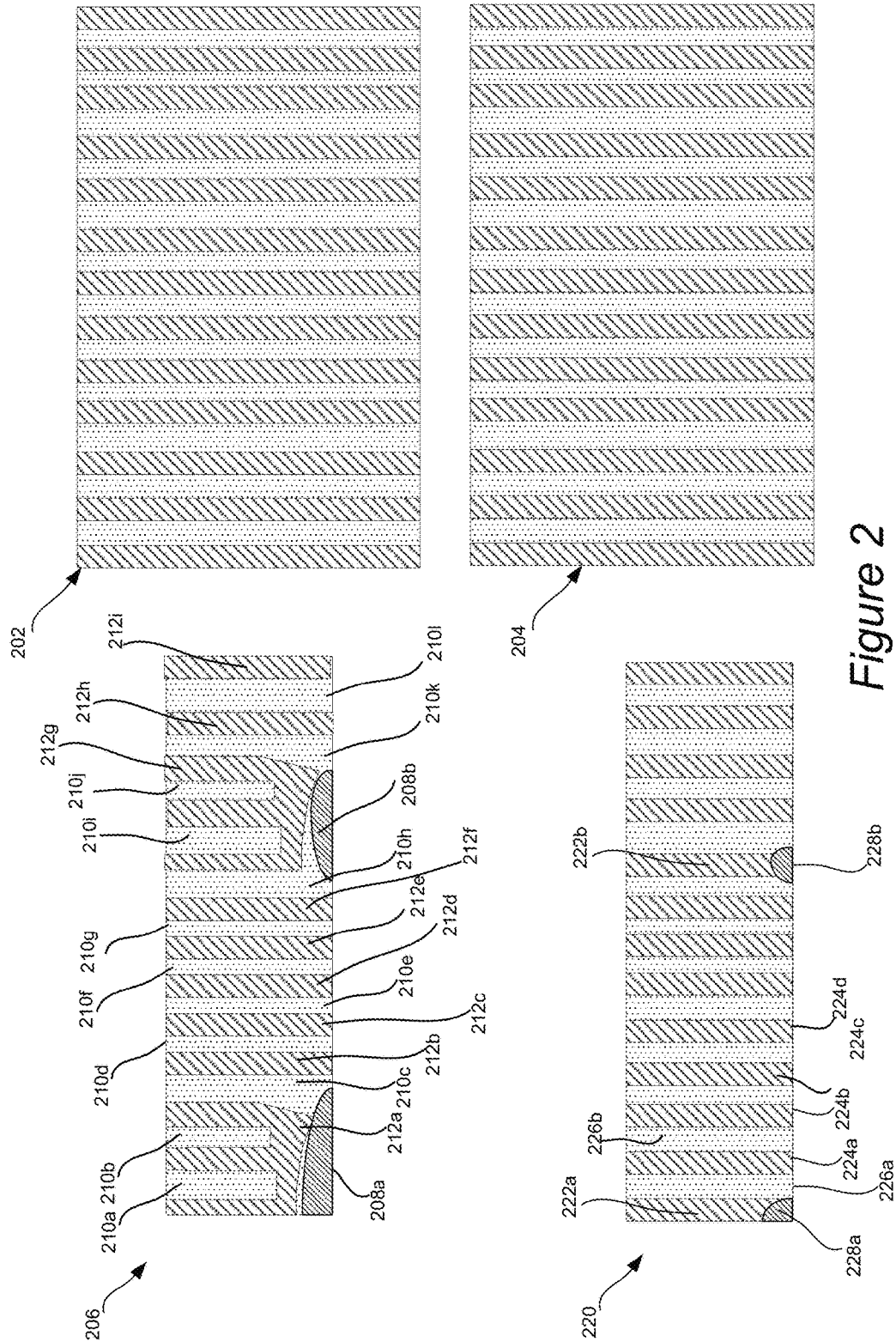

● single measurement area
⸽⸽⸽ measurement site

METHODS AND APPARATUS FOR PATTERNED WAFER CHARACTERIZATION

CROSS-REFERENCE TO RELATED APPLICATIONS

This application claims the benefit of prior application U.S. Provisional Application No. 61/862,801, filed 6 Aug. 2013 by Thaddeus Gerard Dziura et al. and U.S. Provisional Application No. 61/943,098, filed 21 Feb. 2014 by Thaddeus Dziura et al., which applications are herein incorporated by reference in their entirety for all purposes.

TECHNICAL FIELD OF THE INVENTION

The present invention relates generally to methods and systems for characterization of semiconductor wafers and, more specifically, to characterization of the quality of printed patterns on a semiconductor wafer.

BACKGROUND

Photolithography or optical lithography systems used in the manufacture of integrated circuits have been around for some time. Such systems have proven extremely effective in the precise manufacturing and formation of very small details in the product. In some photolithography systems, a circuit image is written on a substrate by transferring a pattern via a light or radiation beam (e.g., UV or ultraviolet light). For example, the lithography system may include a light or radiation source that projects a circuit image through a reticle and onto a silicon wafer coated with a material sensitive to irradiation, e.g., photoresist. The exposed photoresist typically forms a pattern that after development masks the layers of the wafer during subsequent processing steps, as for example deposition and/or etching.

In one metrology technique, characterization of the quality of printed patterns, such as periodic gratings, on a semiconductor wafer can be determined by collecting critical dimension scanning electron microscope CD-SEM images at each location on the wafer and examining each image for pattern quality. This technique is time consuming (e.g., several hours), and judgments about grating quality may currently be somewhat subjective. The CD-SEM measurement also fails to provide information as to the subsurface defect structure.

In view of the foregoing, improved apparatus and techniques for characterization of printed patterns are desired.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a method of characterizing a plurality of structures of interest on a semiconductor wafer is disclosed. A plurality of spectra signals are measured from a particular structure of interest at a plurality of azimuth angles from one or more sensors of a metrology system. A difference spectrum is determined based on the spectra signals obtained for the azimuth angles. A quality indication of the particular structure of interest is determined and reported based on analyzing the difference spectrum.

In a specific implementation, determining the quality indication of the particular structure is performed without use of a model or extraction of a quantitative feature from such particular structure of interest. In another aspect, the difference spectrum is an average difference of a plurality of differences between the spectra signals at the multiple azimuth angles over a plurality of wavelengths. In a further aspect, the difference spectrum is a highest one of a plurality of differences between the spectra signals at the multiple azimuth angles at a particular one of a plurality of wavelength ranges. In yet another aspect, the particular structure is a grating structure. In this embodiment, theoretical or measured difference spectra are determined for the azimuth angles for a nondefective grating structure, and the average difference is normalized by the theoretical spectral difference to determine a defect quantity.

In another implementation, measuring spectra includes generating a differential model by using two dimensional beam profile reflectometry. In a further aspect, a differential model between an image and best fit of a radially symmetric image with a residual error is determined. It is then determined whether the difference spectra indicate a film or defective structure based on such differential model.

In another aspect, the targets are selected from Directed Self Assembly (DSA) structures, under layer non-Directed Self Assembly (non-DSA) structures, and patterned resist structures. In another embodiment, reference data that quantifies pattern defects are collected using a CD SEM tool. Spectra signals are obtained at the azimuth angles from a training set of pattern structures having known pattern defects. A first relation function is determined between spectra signals measured at different azimuth angles and a residual error, and this first relationship is based on the spectra signals obtained at the azimuth angles from the training set. A second relation function is determined between a residual error and a quantification of pattern defects based on the reference data. The spectra signals measured from the particular structure of interest at the azimuth angles are input to the second relation function to determine a quantification of pattern defects for such particular structure. In a further aspect, the first and second relation functions are based on a data reduction technique applied to the spectra signals and residual errors for the training set and the particular structure.

In another method embodiment, at one or more sensors of a metrology system, a plurality of spectra signals are measured from a plurality of neighboring locations at a measurement site of the film or a structure that is designed to be uniform across the measurement site. An average or mean signal of the spectra signals is determined. A standard deviation of each of the spectra signal is determined at each location from the average or mean signal. A quality indication is determined and reported for each location of the film or structure based on analyzing the standard deviation for such location without use of a model or extraction of a quantitative feature from the film or structure.

In an alternative embodiment, the invention pertains to a system for inspecting or measuring a specimen. This system comprises an illuminator for generating illumination and illumination optics for directing the illumination towards a particular structure at a plurality of azimuth angles. The system also includes collection optics for directing a plurality of spectra signals in response to the illumination at the azimuth angles from the particular structure to a sensor. The system further includes a processor and memory configured for performing any of the above described operations. In a specific implementation, the system is in the form of an elipsometer and includes a polarization state generator for producing a polarized state in the illumination and a polarization state analyzer for analyzing a polarized state of the optical signals. In other embodiments, the system is in the form of a spectroscopic ellipsometer, Mueller matrix spectroscopic ellipsometer, spectroscopic reflectometer, spectroscopic scatterometer, beam profile reflectometer, or beam profile ellipsometer.

These and other aspects of the invention are described further below with reference to the figures.

BRIEF DESCRIPTION OF THE DRAWINGS

FIG. 2 a bridging defect in a DSA line space pattern and a non-defective DSA line space pattern.

DETAILED DESCRIPTION OF EXAMPLE EMBODIMENTS

In the following description, numerous specific details are set forth in order to provide a thorough understanding of the present invention. The present invention may be practiced without some or all of these specific details. In other instances, well known process operations have not been described in detail to not unnecessarily obscure the present invention. While the invention will be described in conjunction with the specific embodiments, it will be understood that it is not intended to limit the invention to the embodiments.

Introduction

Figure 1A:
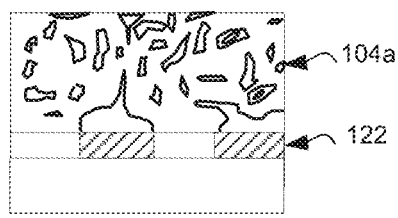
FIGS. 1A-1D are diagrammatic representations of an example DSA process that implements a guide pattern onto which a block copolymer material becomes increasingly self-ordered during an annealing process.
Figure 1B:
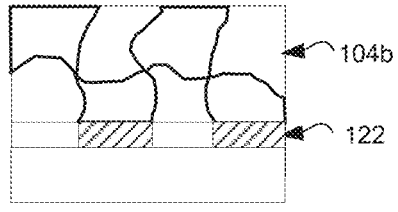
Figure 1C:
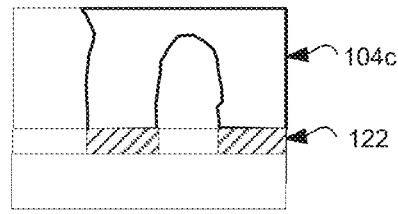
Figure 1D:
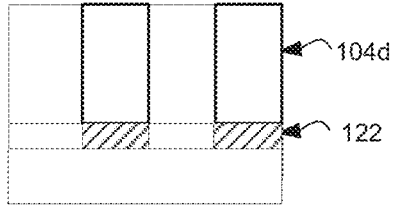

Directed self-assembly (DSA) is currently being explored by many groups as a patterning technology for advanced nodes. FIGS. 1A~1D are diagrammatic representations of a DSA process utilizing a guide pattern 122 onto which a block copolymer material becomes increasingly self-ordered during an annealing process. As shown, block copolymer material 104a initially is disordered with respect the guide pattern 122 in FIG. 1A. After a first duration of annealing, a slightly more ordered block copolymer material 104b forms over the guide pattern 122 as shown in FIG. 1B. After more annealing, a more ordered block copolymer material 104c forms over the guide pattern 122 in FIG. 1C. Finally, an ordered block copolymer material 104d forms over the guide pattern 122 for a particular duration of annealing in FIG. 1D. One of the copolymer components may then be etched (not shown) to obtain a fine grating structure from the remaining copolymer material.

In one of the primary types of DSA processes known as "chemoepitaxy", the quality of the grating manufacture is a sensitive function of the guide pattern dimensional parameters, as well as the chemical properties of the materials. Defects in these gratings can take the form of randomly ordered structures, partially disordered regions, and subsurface bridging of one DSA material below another. FIG. 2 a bridging defect in a DSA line space pattern 206 and a non-defective DSA line space pattern 220. Specifically, DSA line space pattern 206 is formed over an underlying chemical pattern 208a and 208b having non-optimal width. The DSA pattern is disordered due to the suboptimal underlying guide substrate pattern 208a and 208b. For instance, the defective grating 206 includes first copolymer component material that is patterned into incomplete lines 210a, 210b, 210i, and 210j, as well as complete lines 210c, 210d, 210e, 210f, 210g, 210h, 210k, and 210l. The second copolymer component forms defective bridge portions 212a and 212g, as well as lines 212b, 212c, 212d, 212e, 212f, 212h, and 212i.

In contrast, DSA pattern 220 is not defective. Second copolymer component lines 222a and 222b are formed over optimal width substrate portions 228a and 228b. Additional second copolymer component lines (224a~224d), as well as first copolymer component lines (e.g., 226a and 226b), are also formed between such substrate portions 228a and 228b. When the top surface of both the non-defective DSA pattern 220 and defective DSA pattern 206 are imaged with a CD-SEM, the resulting images 202 and 204 are substantially identical. Consequently, the underlying bridge defects of DSA pattern 206 are not detected.

Figure 3:
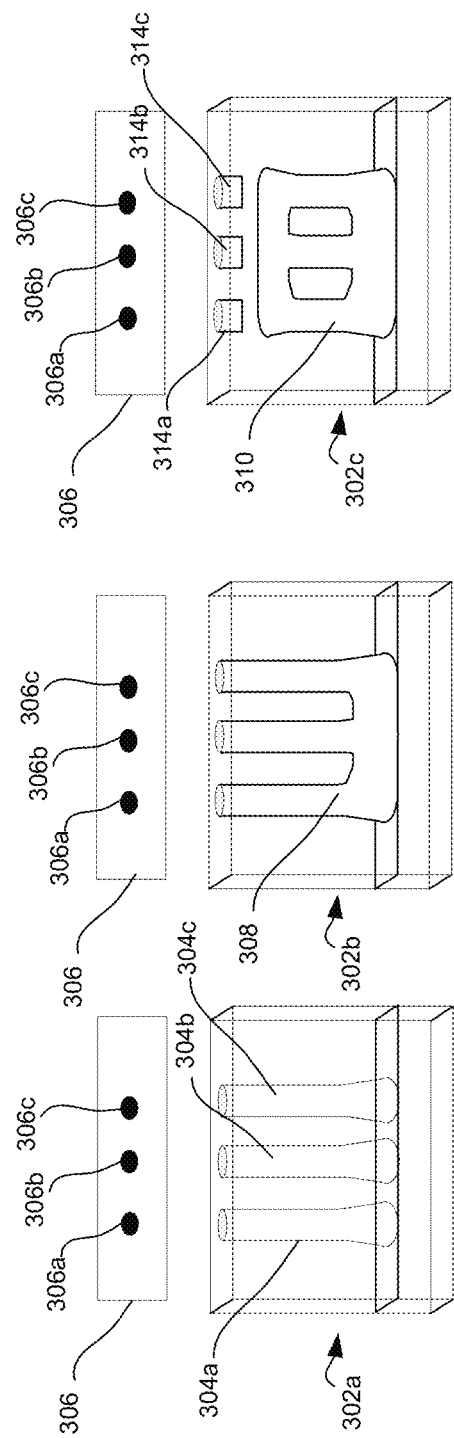
FIG. 3 includes diagrammatic representations of three widely varying DSA patterns and their resulting top view CD-SEM images.

FIG. 3 includes diagrammatic representations of three widely varying DSA patterns 302a, 302b, and 302c. Specifically, DSA pattern 302a is formed from three column structures 304a, 304b, and 304b. DSA pattern 302b is formed from bridged columns structure 308, while DSA pattern 302c is formed from bridged lower portion 310 and disconnected upper column portions 314a, 314b, and 314c. All three structures 302a~302c result in the same top surface CD-SEM image 306 having three column image portions 306a, 306b, and 306c.

In the case of subsurface defects, CD~SEM tools are blind to the defects, without modification of typical measurement conditions and possible damage to the device. It is believed by some that the lack of detection of these subsurface defects poses a serious impediment to high volume manufacturing.

One goal on the part of those currently developing DSA processes is to determine where a well-formed and poor-formed gratings are formed, and where a disordered film is formed. This distinction can depend on the lithography tool exposure and dose that was used to pattern the guide layer at the bottom of the DSA film stack. The azimuthal asymmetry in the optical response of the layer may be used to quantify whether a well ordered grating was formed.

Example Embodiments for Characterizing Patterns:

Certain embodiments of the present invention include apparatus and methods for spectra data collection and signal processing for characterizing the quality of structures of interest on a semiconductor wafer without requiring any modeling. Characterizing the quality can include an indication as to whether a structure of interest is good or poor quality. These techniques allow a simpler and more rapid means of characterizing process yield across an entire wafer based on analyzing the raw spectra signals. In certain embodiments, these techniques are applicable to characterization of the quality of periodic structures (diffraction gratings) and resist or directed self-assembly (DSA) structures, in particular. Besides grating structures, other types of wafer structures of interest can be analyzed for quality. Examples include film, periodic and aperiodic structures, etc.

In certain embodiments, spectra measurements are taken at multiple azimuth angles. In another example, multiple spectra signals are obtained from neighbor measurement locations.

The spectra signals acquired from the measurement sites may include any pairs of the same signal type that can be subtracted from each other or compared with one another. Example signals include, but are not limited to, any type of scatterometry, spectroscopic, ellipsometry, and/or reflectometry signals, including: $\Psi$, $\Delta$, Rs (complex reflectivity of the s polarization), Rp (complex reflectivity of the p polarization), Rs ($|r_s|^2$), Rp ($|r_p|^2$), R (unpolarized reflectivity), $\alpha$ (spectroscopic "alpha" signal), $\beta$ (spectroscopic "beta" signal), and functions of these parameters, such as tan($\Psi P$), cos($\Delta$), ((Rs−Rp)/(Rs+Rp)), Mueller matrix elements ($M_{ij}$), etc. The signals could alternatively or additionally be measured as a function of incidence angle, detection angle, polarization, azimuthal angle of incidence, detection azimuthal angle, angular distribution, phase, or wavelength or a combination of more than one of these parameters. The signals could also be a characterization of a combination of signals, such as an average value of a plurality of any of the above described ellipsometry and/or reflectometry signal types. Other embodiments may use monochromatic or laser light sources where at least one of the signals may be obtained at a single wavelength, instead of multiple wavelengths. The illumination wavelengths could be any range, starting from X-ray wavelengths and going to far infra-red wavelengths.

The difference (or standard deviation) between two (or more) spectra signals can then be directly analyzed to determine whether the measurement site has a good or poor quality without use of a model and without extraction of any feature parameters, such as CD or film thickness. That is, a quality indicator of the measurement site can be based only on the difference between two or more measured spectra signals.

In a grating target example, difference between the spectra may be generally computed, and this difference value can also be determined at various locations across the wafer. At locations where the spectra difference is higher in a relative sense, the probability that a well-formed grating exists is higher, where the grating structure is poor or even disordered, optical measurements will not detect any strong azimuthal asymmetry and the spectral difference between measurements at different azimuth directions will be zero or nearly so.

Figure 4A:
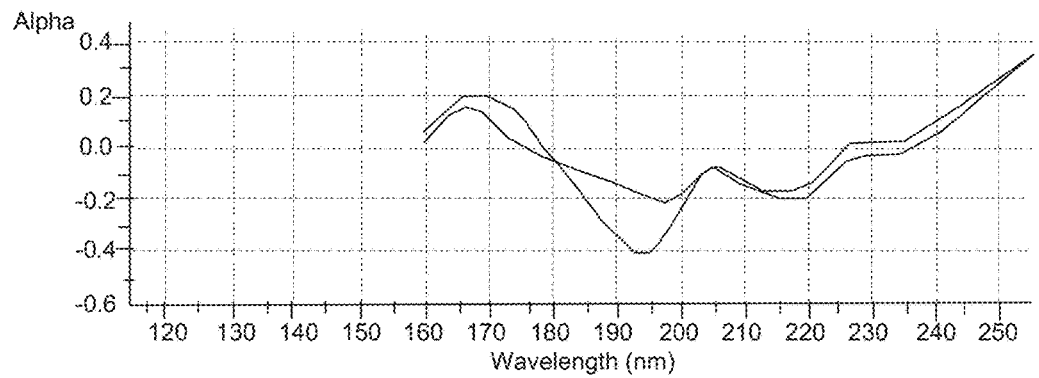
FIG. 4A shows the ellipsometric spectra for an alpha signal, where the grating quality is known to be good.
Figure 4B:
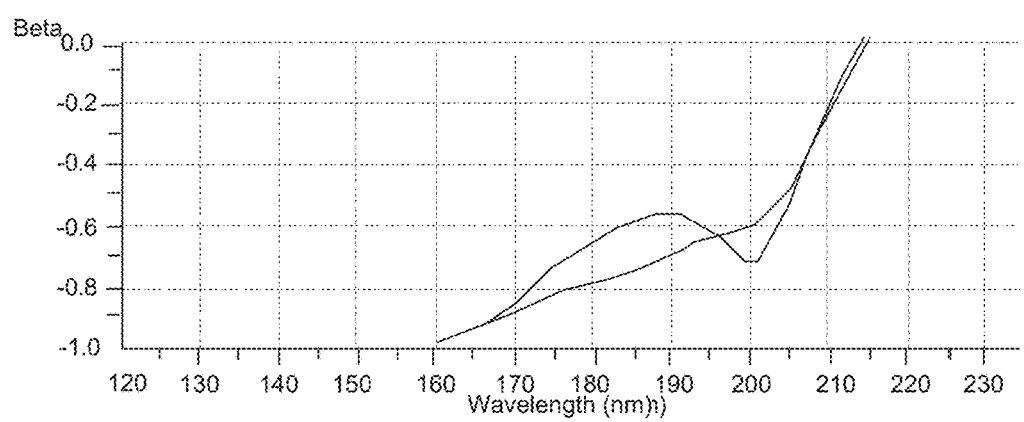
FIG. 4B shows a similar set of spectra for a beta signal, where the grating quality is known to be good.
Figure 5:
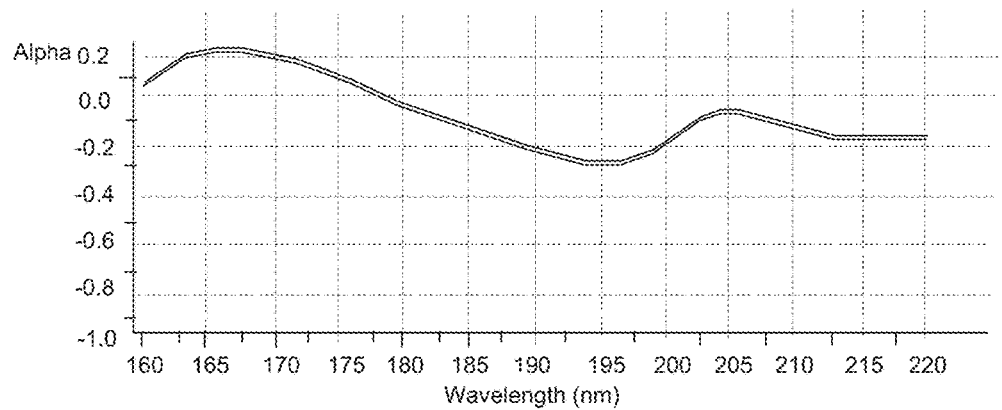
FIG. 5 shows a similar set of spectra for alpha, where the grating quality is known to be poor.

FIG. 4A shows the ellipsometric spectra for alpha ($\alpha$) signals, measured in a same location at two azimuth angles where the grating quality is known to be good. Likewise, FIG. 4B shows a similar set of spectra for a beta ($\beta$) signal, where the grating quality is known to be good. The presence of a high quality grating is evidenced by the separation between the measured spectra at the two azimuth angles. In contrast, FIG. 5 shows a set of spectra for alpha ($\alpha$), where the grating quality is known to be poor. The presence of a poor quality grating is evidenced by the lack of separation between the two measured spectra at the two azimuth angles for the signals. Although the alpha ($\alpha$) signals are only shown for a known poor quality grating, similar results would occur for beta ($\beta$) signals.

Figure 6:
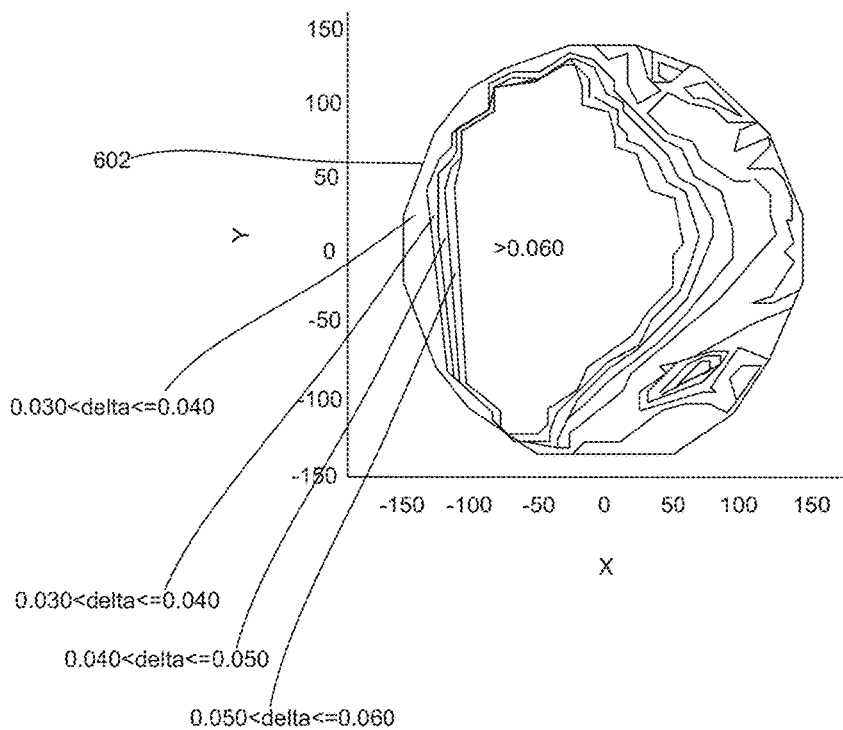
FIG. 6 shows spectra difference (delta) plotted as a function of location on a wafer.

FIG. 6 shows spectra difference (delta) plotted as a function of location on a wafer 602, for a wafer with a process variation from left to right. The areas of high spectra difference between azimuths correlated very well with yield maps measured for the wafer. For example, some contour areas are shown as having delta (or difference between signals) that is greater than 0.060, between 0.050 and 0.60, between 0.050 and 0.040, between 0.040 and 0.030, etc. These difference values can also be indicative of grating quality.

Figure 7:
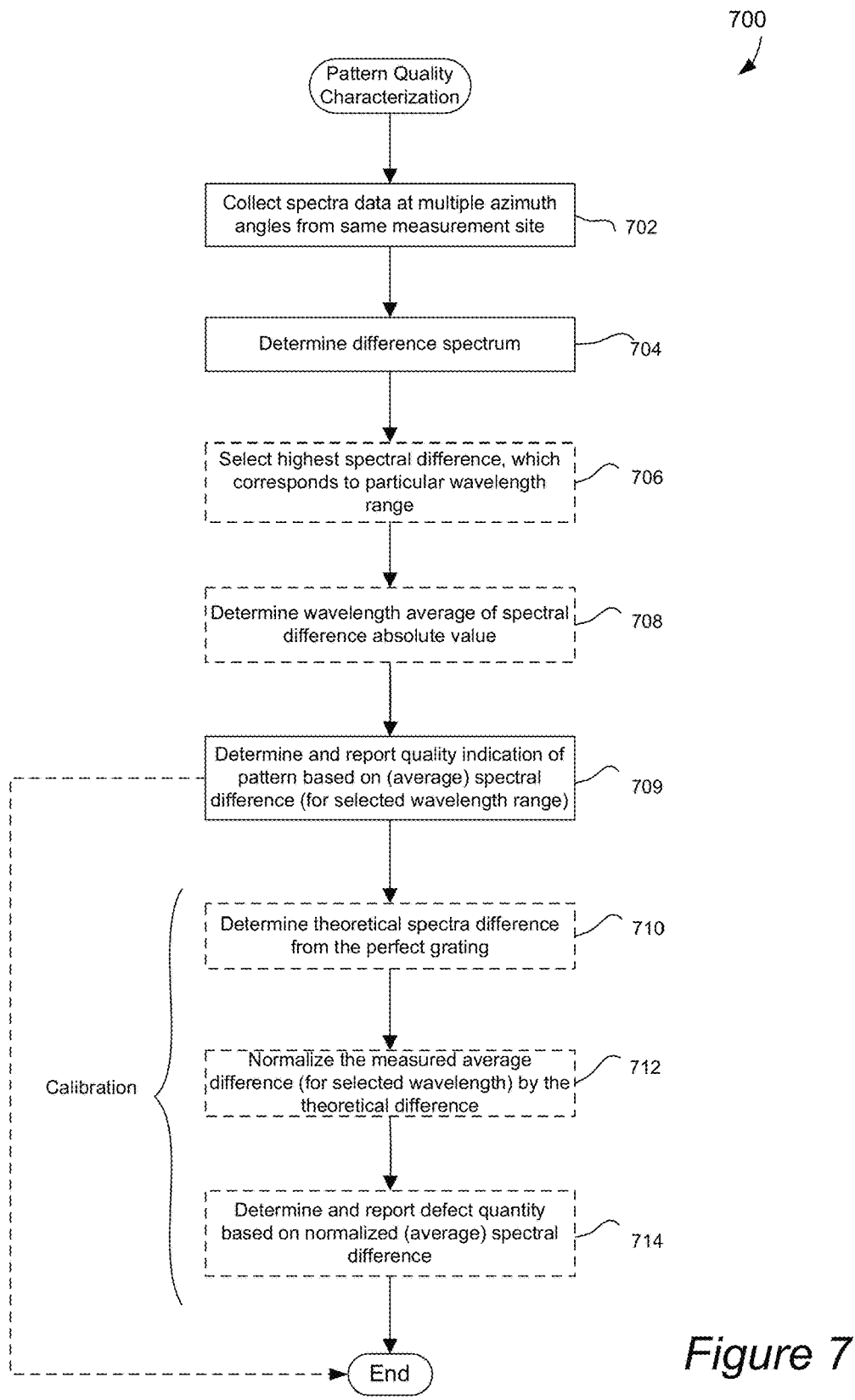
FIG. 7 is a flow chart illustrating a procedure for determining a quality characterization for a wafer pattern in accordance with one embodiment of the present invention.

FIG. 7 is a flow chart illustrating a procedure for determining a quality characterization for a wafer pattern in accordance with one embodiment of the present invention. Spectra data may initially be collected at multiple azimuth angles from the same measurement site in operation 702. In general, the two or more azimuth angles may include any suitable angles, such as angles that are orthogonal to each other for increased sensitivity to grating or pattern defects (although not required). For example, spectra measurements may be obtained at directions perpendicular and parallel to the grating direction.

The measurements may include any suitable spectra radiation signals, such as scatterometry, reflectometry, or ellipsometry signals, including examples described herein. The type of acquired signals may be selected based on signal sensitivity to the structure of interest. For instance, certain wavelengths may be more sensitive to certain particular structure dimensions. The structures of interest may include any patterned or periodic structures, including 2-dimensional and 3-dimensional gratings, dot arrays, etc.

After the spectra are acquired, a difference spectrum may then be determined in operation 704. If there are only two spectra collected for the particular structure of interest, then the spectra signals can be simply subtracted to obtain a difference signal. If there are more than two spectra, any number of techniques may be used to obtain a difference signal. If there are more than two azimuth angles, spectra for each pair of azimuth angles may be subtracted. In one embodiment, differences are obtained for each pair of orthogonal angles. If spectra for each azimuth angle are also obtained at multiple wavelength ranges, the highest spectral difference, which corresponds to a particular one of the wavelength ranges, may then be optionally selected in operation 706. In another example, the difference signals (e.g., at different wavelengths) may be reduced to a single difference value. In the illustrated example, the wavelength average of the spectral difference absolute values may be determined in operation 708. That is, the average of the difference signals for the different wavelengths may be determined to obtain an average difference signal.

The quality indication may be defined based on any suitable difference thresholds or percentage values, for example, as compared to average differences. For instance, difference signals that are higher than a predefined threshold may result in a quality indication of "good", otherwise, differences signals that are lower or equal to the predefined threshold may result in a "poor" quality indication. For the example shown in FIG. 6, the threshold may be set to delta larger than 0.06 as indicative of a good quality grating.

A pattern that is in the form of a good perfect grating, for example, tends to produce a large difference in spectra signals measured at different azimuth angles. As a grating structure becomes more defective, the measured signal difference becomes diminished and resembles a uniform film response, which has a difference of zero at different azimuth angles. That is, a difference value that is between a maximum difference value associated with a perfect grating and zero indicates defects for a grating or pattern structure.

A quality indication of the pattern may then be determined and reported based on the spectral difference in operation 709. The quality indication may optionally be based on the wavelength average of the spectral differences (from operation 708) or based on the highest spectral difference for a selected wavelength (from operation 706). The procedure may then end or be repeated for multiple targets.

The above-described quality determination procedure may then be followed with a calibration procedure. A calibration process may optionally be performed to quantify defects for a structure of interest that is deemed to have poor quality. In the illustrated embodiment, the theoretical spectra difference from a perfect grating may also be optionally determined in operation 710. The measured spectra difference is normalized (or calibrated) by the theoretical spectral difference in operation 712. A defect quantity may then be determined and reported based on the normalized spectral difference in operation 714. Similar to the quality determination, the defect quantity may optionally be based on the wavelength average of multiple spectral measurement differences (from operation 708) or based on the highest spectral difference for a selected wavelength (from operation 706). After calibration is performed to quantify defects, the procedure 700 may also be repeated for multiple spectra differences or the procedure may end.

Figure 8:
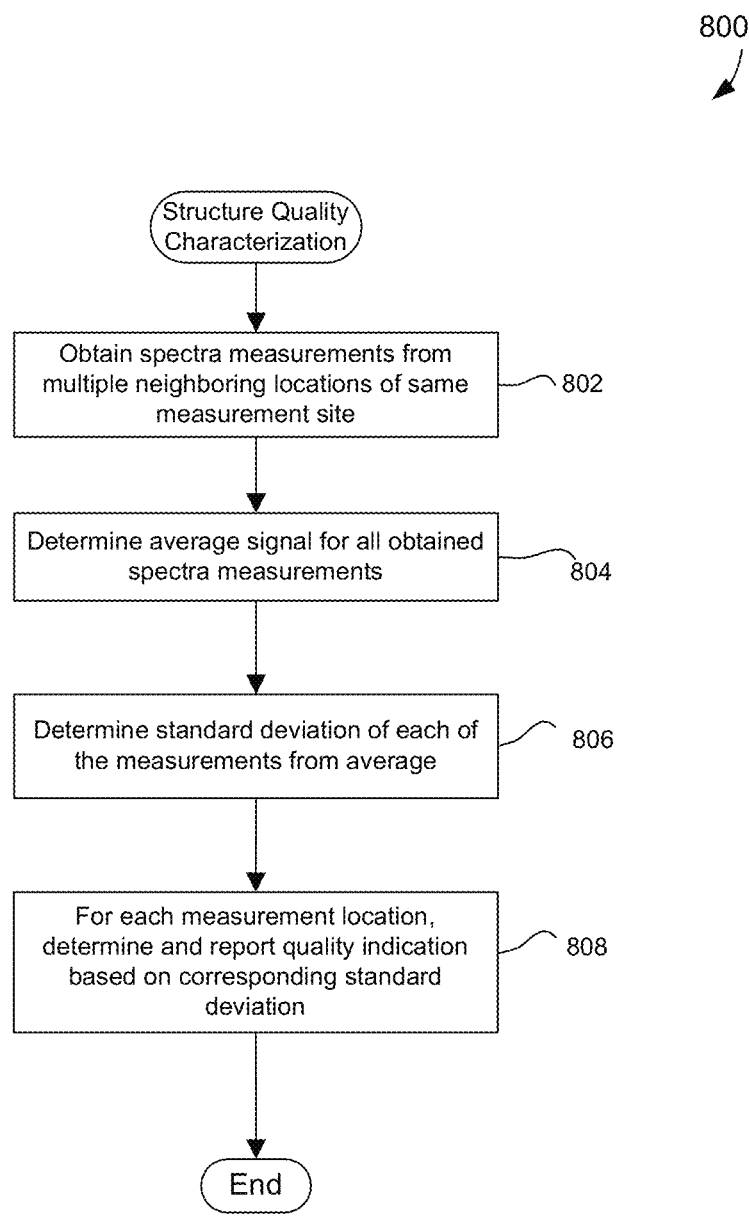
FIG. 8 is a flow chart describing another method of indicating quality on a semiconductor wafer using multiple measurements in a measurement site in accordance with an alternative embodiment of the present invention.
Figure 9:
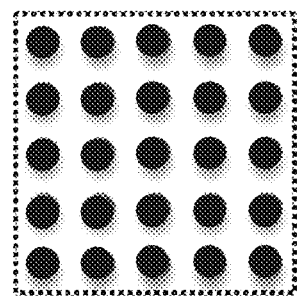
FIG. 9 is a diagrammatic representation of a plurality of neighboring measurement locations of a single measurement site in accordance with one example implementation of the present invention.

Other measurement structures for which quality can be determined based on spectral signal comparison are films. FIG. 8 is a flow chart describing another method 800 of indicating quality on a semiconductor wafer using multiple measurements in a measurement site in accordance with an alternative embodiment of the present invention. FIG. 9 is a diagrammatic representation of a plurality of neighboring measurement locations of a single measurement site in accordance with one example implementation of the present invention. Initially, spectra measurements may be obtained at multiple neighboring locations of a same measurement site in operation 802. The neighboring locations from which measurements are obtained are preferably adjacent to each other without overlapping the actual measurement areas.

An average (or mean) signal for all (or a portion of) the obtained spectra measurements may be determined in operation 804. A standard deviation of each of the measurements from the average (or mean) value is determined in operation 806. For each measurement location, a quality indication can be determined and reported based on the corresponding standard deviation at such measurement location in operation 808. The aforementioned steps may be repeated for multiple sites across the wafer to generate wafer quality maps. This process may also be extended with a calibration procedure to quantify defects as described further herein.

A measurement site for the technique of FIG. 8 may include any suitable one or more structures of interest, such as a grating or film structure, which are expected to be uniform. For example, a grating that fills the entire measurement site would be expected to be uniform at different measurement locations across the measurement site area unless such grating is defective. Likewise, a film that fills the measurement site would be expected to have a same thickness (and uniformity) across the measurement site and result in the same spectra signal at different measurement locations in such measurement site. The more defects that are present in both examples; the larger the spectral difference will be. Thus, this technique is applicable to regular structures, which may include films, 2D and 3D gratings, dot (or any other type) arrays, periodic structures, etc.

Figure 10A:
FIGS. 10A and 10B show two-dimensional beam profile reflectometry (2DBPR) signal residuals for low quality wafers and high quality wafers, respectively, in accordance with one example implementation of the present invention.
Figure 10B:
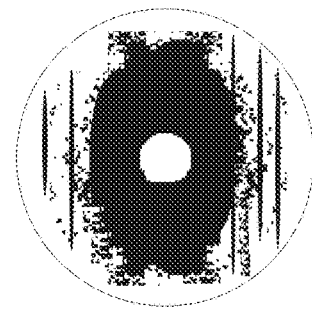

FIGS. 10A and 10B show two-dimensional beam profile reflectometry (2DBPR) signal residuals (or difference signals) for low quality wafers (FIG. 10A) and high quality wafers (FIG. 10B). While the examples in FIG. 10A and FIG. 10B use angle-resolved signal, the same approach is also applicable for wavelength-resolved spectra. Certain techniques of the present invention can be considered "model-less" since no assumptions about measured semiconductor patterns are made. Additionally, no quantified values, such as CD, of the structure of interest need be extracted from the measured spectra by comparison to model results.

Certain model-less embodiments of the present invention may be extended by training techniques for known quality structures (e.g., known poor and good gratings). An algorithm based on machine-learning methodology, such as neural networks, may be used to relate measured spectra signals to pre-programmed variations in a test structure, such as the DSA pattern, based on a training set of known structures. That is, a training set with predefined or known variations can be measured to obtain spectra signals to determine a model for relating spectra signals to feature or process variations. After the machine learning operation is completed, feature and process-related parameters can be extracted from spectra signals obtained from structures of interest having unknown characteristics using such model.

In further embodiments, various process parameters are varied. To illustrate, when the guide pattern pitch is varied within the same wafer or on different wafers, the dimensional properties of the DSA pattern are affected. Alternatively, varying thickness of the block copolymer layer can be a part of the design of experiments (DOE) training set. Process parameter variations, such as anneal temperature, may be used as another way to create a DOE training set, e.g., different wafers are processed at different anneal temperatures.

After a DOE training set is created, targets that were fabricated using different process conditions can be measured to obtain spectra, such as particular signal type from a single measurement site at two azimuth angles or a particular signal type from multiple measurement sites, which are then processed as a part of the training algorithms. To determine dimensional parameters (such as profile characteristics (bottom or top CD, sidewall angle, etc.) for the training set, these targets from the training set may be characterized by a reference metrology that can be destructive, e.g. cross-section TEM or by atomic force microscopy (AFM) or CD-SEM. The known feature parameters may simply include indications as to poor or good quality, rather than specific metrology values.

Deviation from ideal or desired DSA pattern may also be characterized, e.g., by training to correlate measured signals to in-spec or out-of-spec (or good vs. poor quality) DSA patterns. For example, a DSA structure with bridging can generate nonsymmetrical signatures in angle-resolved signals or cross-polarized signals that would not be generated by ideal patterns. The asymmetry levels and angular or spectral content of such signals can be related to the density of bridging defects (or other defect types) in the measured area. By using a training methodology, one can train a feature extractor process to analyze in-spec vs. out-of-spec patterns, depending on the spectra that such structures produce (e.g. such spectra as two azimuth angles or from multiple measurement sites). Spectra from unknown structures can then be input to the trained feature extractor. The feature extractor output can be used to adjust process parameters to compensate for process drift occurring in the DSA patterning over time, like in an APC (advanced process control) system.

In a development use case, as opposed to production use case, chemistry of block copolymers may also be varied to achieve optimum patterning dimensions and roughness properties. These properties can be varied in a DOE (design of experiment) set and characterized using any of the training approaches described above.

Figure 11:
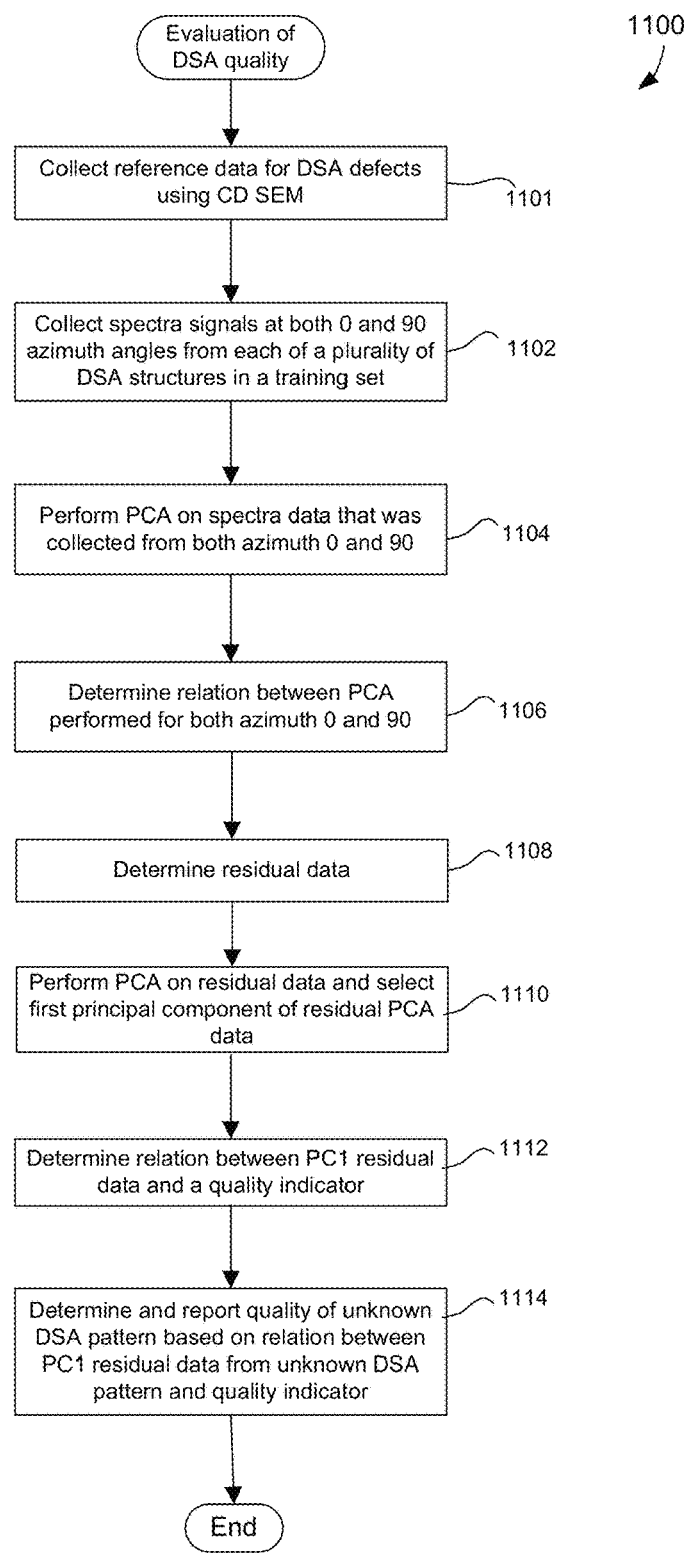
FIG. 11 illustrates a method of evaluating the DSA grating quality by using differential models in accordance with an alternative embodiment of the present invention.

In one illustrative example, the method of FIG. 7 can be implemented in a differential model as is described in FIG. 11. For example, a differential model can be determined for a zero azimuth angle (AZ0) related to a 90° azimuth angle (Az90): Az0=f(Az90)+err, where f( ) is a function that best fits the Az90 signals to the Az0 signals and err represents the residual errors between the Az90 and Az0 signals. A minimum and maximum residual error for the entire wafer can be determined. When the Az0 and Az90 signals are very similar, then this residual error will be small (minErr)—at the level of random noise. This small minErr corresponds to poorly formed DSA structures. In contrast, large err (maxErr) corresponds to well-formed DSA structures. The error between minErr and maxErr can be used to evaluate the relative quality of the DSA grating.

FIG. 11 illustrates a method 1100 of evaluating DSA grating quality by using a differential model in accordance with an alternative embodiment of the present invention. Initially, reference data for DSA defects may be collected from reference DSA structures using CD SEM or other metrology tools in operation 1101. That is, the CD SEM may be used to classify a plurality of DSA reference structures as having a poor or good quality (or being defective or non-defective) and different number of defects. This reference data includes quality indications and/or defect count for known DSA structures and their corresponding spectra data. The spectra reference data will include the same type of signals as collected for the training set below.

Spectra signals at both 0 and 90° azimuth angles may be collected from each of a plurality of DSA structures from a training set in operation 1102. While the Illustrative example describes orthogonal azimuth angles, other angles can be used. However, the azimuth pairs are at different angular positions. Any type of spectra signals, such as spectroscopic data, may be collected. The training set DSA structures will contain different number of defects.

Principal component analysis (PCA) may then be performed on the spectra data from the training set at both the 0 and 90° azimuth angles in operation 1104. Any suitable feature extraction technique, besides PCA, may be implemented so as to extract a feature from the spectra signal pairs having the best information, while reducing the dataset. Other example automated feature extract techniques include Independent Component Analysis (ICA), Local Linear Embedding (LLE) algorithm, etc.

A relation between the PCA's performed for both azimuth angles may be determined in operation 1106. In general, the relation will represent a function that best relates the PCA data from both azimuth angles. The residual data may then be determined in operation 1108. The residual data is generally the difference between the best fit function that relates the PCA data from both azimuth angles. PCA may then be performed on the residual data and one or several principal components (e.g. the first principal component PC1) of the PCA residual data can be selected in operation 1110.

A relation between the PC1 residual data and the reference data may then be determined in operation 1112. For instance, PC1 residual data may be compared to the PC1 data for the reference data that was obtained from known DSA patterns having known defect quality (e.g., poor or good quality and/or number of defects), and a model that relates PC1 to quality may then be determined. The DSA pattern quality of an unknown DSA pattern can then be determined based on the relation between the PC1 residual data determined from the spectra collected from such unknown DSA and quality in operation 1114.

Although the following example embodiments are described in terms of using the first principal component resulting from a PCA transformation in order to extract information pertaining to a quality parameter, other embodiments may utilize other feature extraction results or techniques. For instance, the first and second principal components as determined via PCA may be used. Any number of principal components may be selected based on the particular requirements of the application. In yet another example, the output from another feature extraction tool, such as ICA or LLE, may be used.

In a PCA embodiment, the extracted feature corresponds to a transformation of the signal dataset onto a different coordinate system and selection of a particular dimension (or direction or projection direction) of such new coordinate system along which the transformed dataset has the most variation, which provides the most information with respect to feature quality. The first principal component corresponds to a transformed direction or dimension of the PCA-transformed dataset that is found to have the most variation. The second principal component has the second most variation, etc.

In general, the aforementioned methods may be calibrated to determine quantitative feature and/or process parameter values. For instance, multiple points of CD-SEM measurements can be taken in order to establish relationship between the number of defects and the error:

NumberOfDefects=Cal(err) or

NumberOfDefects=Cal(Az0−f(Az90)), where Cal( ) is the calibration function obtained by CD-SEM reference measurement sites.

The signals used for creating the differential models can be the raw signals (e.g., alpha, beta) or components of the raw signals obtained by PCA, independent component analysis (ICA), local linear embedding (LLE) or other feature extraction methods.

In another illustrative model example, a 2DBPR Differential model is generated by the measurements. A 2DBPR image is radially symmetric when the measured sample resembles film and non-radially symmetric when the sample has some periodic structure. Using this feature, a radially symmetric surface can be fit to the 2DBPR image.

$$Img = f(Img) + err,$$

where f( ) is the radially symmetric function that fits the image best and "err" is the residual errors corresponding to the asymmetric portion. An asymmetric portion can mean the image is at least partially not radial symmetric and is a defective film.

In the similar way as in the non 2DBPR case, the residual errors can be used to evaluate the level of defects and with calibration, the number of defects could be determined. As in the non 2DBPR case, components of the 2DBPR image can be used, instead of raw signals. In both cases, standard deviation, max value, mean, or the distribution of the errors can be used as a metric of DSA grating quality.

In another illustrative model, a technique can include isolation of the effects (de-correlate) of under layer variations when applied to multiple targets. A DSA target and a target without the DSA layer, but with the same underlayers, can be used. The following cases can be used for underlayer decorrelation:

1. Use the combined signals of two or more targets to extract the significant components, and
2. Use differential models for residuals: residuals=$S_{dsa}$ − f($S_{ul}$), where $S_{dsa}$ is the signals from DSA target and $S_{ul}$ is the signals from the underlayer target and f( ) is the function that best fits $S_{ul}$ to $S_{dsa}$.

After the underlayer decorrellation is applied, any of the above-described DSA differential models can be applied for DSA defect measurement.

Certain techniques of the present invention can enable a significant time savings for characterizing pattern quality for resist or DSA patterns, and reduce the cost of developing and optimizing patterning processes.

Any suitable combination of hardware and/or software may be used to implement any of the above described techniques. In a general example, a metrology tool may comprise an illumination system which illuminates a target, a collection system which captures relevant information provided by the illumination system's interaction (or lack thereof) with a target, device or feature, and a processing system which analyzes the information collected using one or more algorithms. Metrology tools can generally be used to measure various radiation signals pertaining to structural and material characteristics (e.g., material composition, dimensional characteristics of structures and films such as film thickness and/or critical dimensions of structures, overlay, etc.) associated with various semiconductor fabrication processes. These measurements can be used to facilitate process controls and/or yield efficiencies in the manufacture of semiconductor dies.

The metrology tool can comprise one or more hardware configurations which may be used in conjunction with certain embodiments of this invention. Examples of such hardware configurations include, but are not limited to, the following: Spectroscopic ellipsometer (SE), SE with multiple angles of illumination, SE measuring Mueller matrix elements (e.g. using rotating compensator(s)), single-wavelength ellipsometers, beam profile ellipsometer (angle-resolved ellipsometer), beam profile reflectometer (angle-resolved reflectometer), broadband reflective spectrometer (spectroscopic reflectometer), single-wavelength reflectometer, angle-resolved reflectometer, imaging system, and scatterometer (e.g. speckle analyzer)

Figure 12:
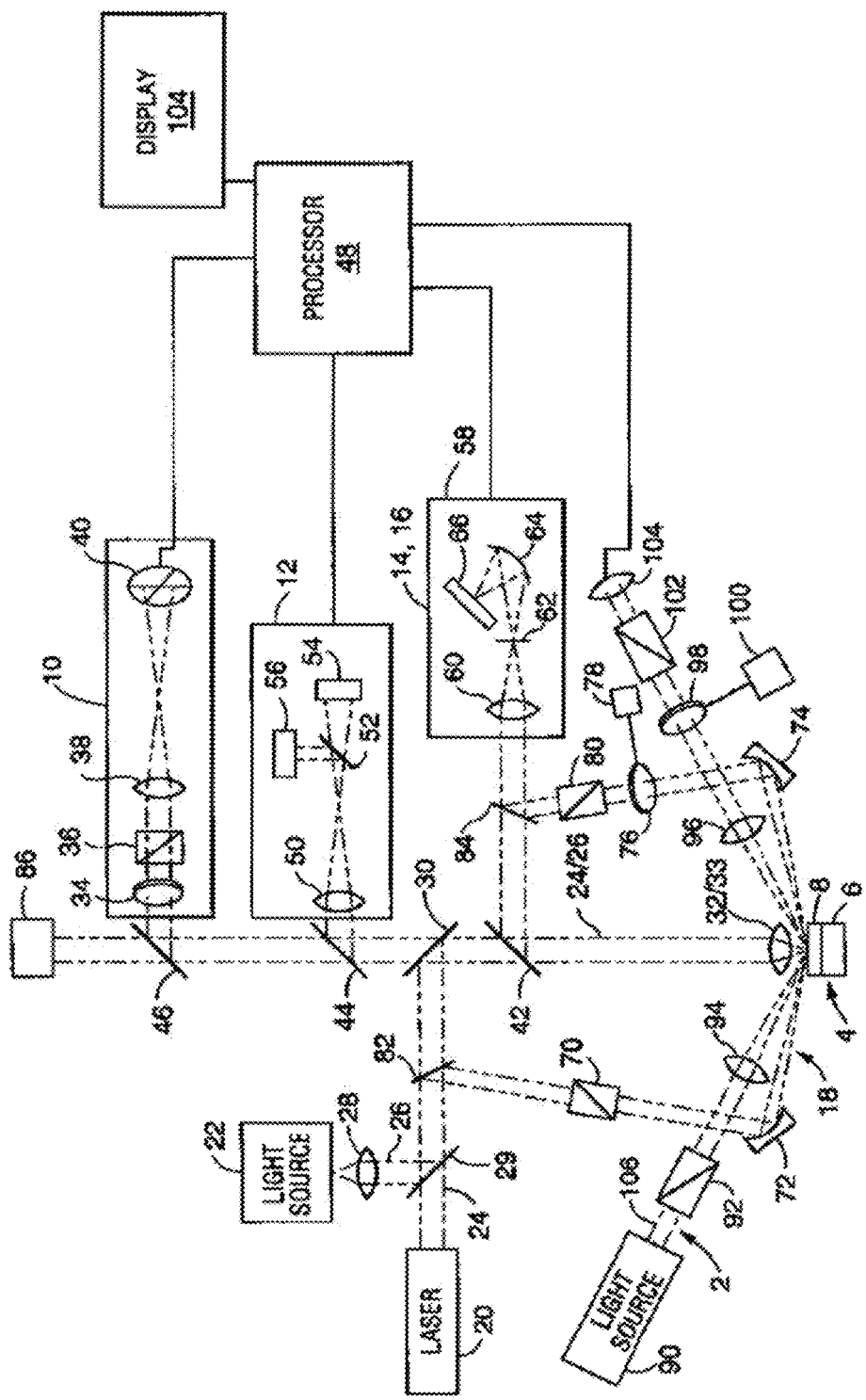
FIG. 12 illustrates an example metrology system in accordance with one embodiment of the present invention.

The hardware configurations can be separated into discrete operational systems. On the other hand, one or more hardware configurations can be combined into a single tool. One example of such a combination of multiple hardware configurations into a single tool is further illustrated and described U.S. Pat. No. 7,933,026, which patent is herein incorporated by reference in its entirety for all purposes. FIG. 12 shows, for example, a schematic of an exemplary metrology tool that comprises: a) a broadband SE (e.g., 18); b) an SE (e.g., 2) with rotating compensator (e.g., 98); c) a beam profile ellipsometer (e.g., 10); d) a beam profile reflectometer (e.g., 12); e) a broadband reflective spectrometer (e.g., 14); and f) a deep ultra-violet reflective spectrometer (e.g., 16). In addition, there are typically numerous optical elements (e.g., 92, 72, 94, 70, 96, 74, 76, 80, 78, 98, 100, 102, 104, 32/33, 42, 84, 60, 62, 64, 66, 30, 82, 29, 28, 44, 50, 52, 54, 56, 46, 34, 36, 38, 40, and 86) in such systems, including certain lenses, collimators, mirrors, quarter-wave plates, polarizers, detectors, cameras, apertures, and/or light sources. The wavelengths for the optical systems can vary from about 120 nm to 3 microns. The azimuth angle for the optical systems can also vary. For non-ellipsometer systems, signals collected can be polarization-resolved or unpolarized.

FIG. 12 provides an illustration of multiple metrology heads integrated on the same tool. However, in many cases, multiple metrology tools are used for measurements on a single or multiple metrology targets. Several embodiments of multiple tool metrology are further described, e.g., in U.S. Pat. No. 7,478,019 by Zangooie et al, entitled "Multiple tool and structure analysis", which patent is incorporated herein by reference in its entirety for all purposes.

The illumination system of certain hardware configurations may include one or more light sources. The one or more light sources may generate light having only one wavelength (e.g., monochromatic light), light having a number of discrete wavelengths (e.g., polychromatic light), light having multiple wavelengths (e.g., broadband light), and/or light that sweeps through wavelengths, either continuously or hopping between wavelengths (e.g., tunable sources or swept sources). Examples of suitable light sources are: a white light source, an ultraviolet (UV) laser, an arc lamp or an electrode-less lamp, a laser sustained plasma (LSP) source, for example, those commercially available from Energetiq Technology, Inc. of Woburn, Mass., a supercontinuum source (such as a broadband laser source) such as those commercially available from NKT Photonics Inc. of Morganville, N.J., or shorter-wavelength sources such as x-ray sources, extreme UV sources, or some combination thereof. The light source(s) may also be configured to provide light having sufficient brightness, which in some cases may be a brightness greater than about 1 W/(nm cm2 Sr). The metrology system may also include a fast feedback to the light source for stabilizing its power and wavelength. Output of the light source can be delivered via free-space propagation, or in some cases delivered via optical fiber or light guide of any type.

In turn, one or more detectors or spectrometers are configured to receive via a collection optical elements illumination reflected or otherwise scattered from the surface of the specimen 4. Suitable sensors include charged coupled devices (CCD), CCD arrays, time delay integration (TDI) sensors, TDI sensor arrays, photomultiplier tubes (PMT), and other sensors. Measured spectra or detected signal data (as a function of position, wavelength, polarization, azimuth angle, etc.) may be passed from each detector to the processor system 48 for analysis.

It should be recognized that the various steps described throughout the present disclosure may be carried out by a single processor system 48 or, alternatively, a multiple processor system 48. Moreover, different subsystems of the system of FIG. 12, such as the spectroscopic ellipsometer, may include a computer system suitable for carrying out at least a portion of the steps described herein. Therefore, the aforementioned description should not be interpreted as a limitation on the present invention but merely an illustration. Further, the one or more processor system 48 may be configured to perform any other step(s) of any of the method embodiments described herein.

In addition, the processor system 48 may be communicatively coupled to a detector system in any manner known in the art. For example, the one or more processor system 48 may be coupled to computing systems associated with the detector system. In another example, the detector system may be controlled directly by a single computer system coupled to processor system 48.

The processor system 48 of the metrology system may be configured to receive and/or acquire data or information from the subsystems of the system by a transmission medium that may include wireline and/or wireless portions. In this manner, the transmission medium may serve as a data link between the processor system 48 and other subsystems of the system of FIG. 12.

Processor system 48 of the integrated metrology system may be configured to receive and/or acquire data or information (e.g., measurement spectra, difference signals, statistical results, reference or calibration data, training data, models, extracted features or transformation results, transformed datasets, curve fittings, qualitative and quantitative results, etc.) from other systems by a transmission medium that may include wireline and/or wireless portions. In this manner, the transmission medium may serve as a data link between the processor system 48 and other systems (e.g., memory on-board metrology system, external memory, reference measurement source, or other external systems). For example, processor system 48 may be configured to receive measurement data from a storage medium (e.g., internal or external memory) via a data link. For instance, spectral results obtained using the detection system may be stored in a permanent or semipermanent memory device (e.g., internal or external memory). In this regard, the spectral results may be imported from on-board memory or from an external memory system. Moreover, the processor system 48 may send data to other systems via a transmission medium. For instance, qualitative and/or quantitative results determined by processor system 48 may be communicated and stored in an external memory. In this regard, measurement results may be exported to another system.

Processor system 48 may include, but is not limited to, a personal computer system, mainframe computer system, workstation, image computer, parallel processor, or any other device known in the art. In general, the term "processor system" may be broadly defined to encompass any device having one or more processors, which execute instructions from a memory medium. Program instructions implementing methods such as those described herein may be transmitted over a transmission medium such as a wire, cable, or wireless transmission link. Program instructions may be stored in a computer readable medium (e.g., memory). Exemplary computer-readable media include read-only memory, a random access memory, a magnetic or optical disk, or a magnetic tape.

The metrology tool may be designed to make many different types of measurements related to semiconductor manufacturing. Certain embodiments of the invention for determining quality and/or quantitative values may utilize such measurements. Additional metrology techniques for determining specific target characteristics may also be combined with the above-described quality determination techniques. For example, in certain embodiments the tool may measure spectra and determine characteristics of one or more targets, such as quality and defect quantity values, critical dimensions, overlay, sidewall angles, film thicknesses, process-related parameters (e.g., focus and/or dose). The targets can include certain regions of interest that are periodic in nature, such as for example gratings in a memory die. Targets can include multiple layers (or films) whose thicknesses can be measured by the metrology tool. Targets can include target designs placed (or already existing) on the semiconductor wafer for use, e.g., with alignment and/or overlay registration operations. Certain targets can be located at various places on the semiconductor wafer. For example, targets can be located within the scribe lines (e.g., between dies) and/or located in the die itself. In certain embodiments, multiple targets are measured (at the same time or at differing times) by the same or multiple metrology tools as described in U.S. Pat. No. 7,478,019. The data from such measurements may be combined. Data from the metrology tool may be used in the semiconductor manufacturing process, for example, to feed-forward, feed-backward and/or feed-sideways corrections to the process (e.g. lithography, etch) and therefore, might yield a complete process control solution.

As semiconductor device pattern dimensions continue to shrink, smaller metrology targets are often required. Furthermore, the measurement accuracy and matching to actual device characteristics increase the need for device-like targets as well as in-die and even on-device measurements. Various metrology implementations have been proposed to achieve that goal. For example, focused beam ellipsometry based on primarily reflective optics is one of them and described in the patent by Piwonka-Corle et al. (U.S. Pat. No. 5,608,526, "Focused beam spectroscopic ellipsometry method and system"). Apodizers can be used to mitigate the effects of optical diffraction causing the spread of the illumination spot beyond the size defined by geometric optics. The use of apodizers is described in the patent by Norton, U.S. Pat. No. 5,859,424, "Apodizing filter system useful for reducing spot size in optical measurements and other applications." The use of high-numerical-aperture tools with simultaneous multiple angle-of-incidence illumination is another way to achieve small-target capability. This technique is described, e.g. in the patent by Opsal et al, U.S. Pat. No. 6,429,943, "Critical dimension analysis with simultaneous multiple angle of incidence measurements."

Other measurement examples may include measuring the composition of one or more layers of the semiconductor stack, measuring certain defects on (or within) the wafer, and measuring the amount of photolithographic radiation exposed to the wafer. In some cases, metrology tool and algorithm may be configured for measuring non-periodic targets, see e.g. "The Finite Element Method for Full Wave Electromagnetic Simulations in CD Metrology Using Scatterometry" by P. Jiang et al (U.S. 61/830,536, K-T disclosure P4063) or "Method of electromagnetic modeling of finite structures and finite illumination for metrology and inspection" by A. Kuznetsov et al. (U.S. 61/761,146 or KT disclosure P4082).

Measurement of parameters of interest can also involve a number of algorithms. For example, optical interaction of the incident beam with the sample can be modeled using EM (electro-magnetic) solver and uses such algorithms as RCWA, FEM, method of moments, surface integral method, volume integral method, FDTD, and others. The target of interest can usually be modeled (parameterized) using a geometric engine, or in some cases, process modeling engine or a combination of both. The use of process modeling is described in "Method for integrated use of model-based metrology and a process model," by A. Kuznetsov et al. (U.S. 61/738,760, P4025). A geometric engine may be implemented, for example, in AcuShape software product of KLA-Tencor of Milpitas, Calif.

Collected data can be analyzed by a number of data fitting and optimization techniques an technologies including libraries, Fast-reduced-order models; regression; machine-learning algorithms such as neural networks, support-vector machines (SVM); dimensionality-reduction algorithms such as, e.g., PCA (principal component analysis), ICA (independent component analysis), LLE (local-linear embedding); sparse representation such as Fourier or wavelet transform; Kalman filter; algorithms to promote matching from same or different tool types, and others.

Collected data can also be analyzed by algorithms that do not include modeling, optimization and/or fitting e.g. provisional patent application 61/745981, which is incorporated herein by reference, and as described herein.

Computational algorithms are usually optimized for metrology applications with one or more approaches being used such as design and implementation of computational hardware, parallelization, distribution of computation, load-balancing, multi-service support, dynamic load optimization, etc. Different implementations of algorithms can be done in firmware, software, FPGA, programmable optics components, etc.

The data analysis and fitting steps may be used to pursue one of the following goals: measurement of quality, defect number, CD, SWA, shape, stress, composition, films, bandgap, electrical properties, focus/dose, overlay, generating process parameters (e.g., resist state, partial pressure, temperature, focusing model), and/or any combination thereof; modeling and/or design of metrology systems; and modeling, design, and/or optimization of metrology targets.

Certain embodiments of the present invention presented here generally address the field of semiconductor metrology and process control, and are not limited to the hardware, algorithm/software implementations and architectures, and use cases summarized above.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. Accordingly, the present embodiments are to be considered as illustrative and not restrictive, and the invention is not to be limited to the details given herein.

What is claimed is:

1. A method of characterizing a plurality of structures of interest on a semiconductor wafer, the method comprising:
measuring a plurality of spectra signals from a particular location of a particular structure at a plurality of azimuth angles from one or more sensors of a metrology system, wherein the particular structure is a grating structure that was formed by a semiconductor manufacturing process;
determining a difference amount between the spectra signals obtained for the azimuth angles;
if the difference amount is above a predetermined threshold, determining and reporting that the particular structure does not contain a defect; and
if the difference amount is equal to or lower than the predetermined threshold or equal to zero, determining and reporting that the particular structure contains a defect, wherein such defect is below a surface of the particular structure.

2. The method of claim 1, wherein determining that the particular structure contains or does not contain a defect is performed without use of a model or extraction of a quantitative feature value from such particular structure.

3. The method of claim 1, wherein the difference amount is an average difference of a plurality of differences between the spectra signals at the azimuth angles over a plurality of wavelengths.

4. The method of claim 3, the method further comprising:
determining theoretical or measured difference amounts between spectra signals for the azimuth angles for a nondefective grating structure; and
normalizing the average difference by the theoretical or measured difference amounts to determine a defect quantity.

5. The method of claim 1, wherein the difference amount is a highest one of a plurality of differences between the spectra signals at the azimuth angles at a particular one of a plurality of wavelength ranges.

6. The method of claim 1, wherein measuring spectra includes generating a differential model by using two dimensional beam profile reflectometry.

7. The method of claim 6, further comprising determining a differential model between an image and best fit of a radially symmetric image with a residual error and determining whether the difference spectra indicate a film or defective structure based on such differential model.

8. The method of claim 1, wherein the particular structure is selected from a Directed Self Assembly (DSA) structure, under layer non-Directed Self Assembly (non-DSA) structure, or patterned resist structure.

9. The method of claim 1, wherein the defect is a subsurface defect.

10. The method of claim 9, wherein the particular structure is a Directed Self Assembly (DSA) structure, wherein correcting the particular structure and/or correcting the manufacturing process comprises correcting a chemoepitaxy of the DSA structure.

11. The method of claim 9, wherein the particular structure is a Directed Self Assembly (DSA) structure, wherein correcting the particular structure and/or correcting the manufacturing process comprises correcting a photolithography process' exposure and/or dose for forming the DSA structure.

12. A method of characterizing a plurality of structures of interest on a semiconductor wafer, the method comprising:
measuring a plurality of spectra signals from a particular structure of interest at a plurality of azimuth angles from one or more sensors of a metrology system;
determining a difference spectrum based on the spectra signals obtained for the azimuth angles;
determining and reporting a quality indication of the particular structure of interest based on analyzing the difference spectrum;
collecting reference data that quantifies pattern defects using a CD SEM tool;
obtaining spectra signals at the azimuth angles from a training set of pattern structures having known pattern defects;
determining a first relation function between spectra signals measured at different azimuth angles and a residual error, wherein the first relationship is based on the spectra signals obtained at the azimuth angles from the training set;

determining a second relation function between a residual error and a quantification of pattern defects based on the reference data; and inputting the spectra signals measured from the particular structure of interest at the azimuth angles into the second relation function to determine a quantification of pattern defects for such particular structure.

13. The method of claim 12, wherein the first and second relation functions are based on a data reduction technique applied to the spectra signals and residual errors for the training set and the particular structure.

14. A semiconductor metrology system, comprising:
an illuminator for generating illumination;
illumination optics for directing the illumination towards a particular location of a particular structure at a plurality of azimuth angles, wherein the particular structure is a grating structure that was formed by a semiconductor manufacturing process;
collection optics for directing a plurality of spectra signals in response to the illumination at the azimuth angles from the particular structure to a sensor;
the sensor for acquiring the plurality of spectra signals from the particular structure for the azimuth angles; and
a processor and memory configured for performing the following operations:
determining a difference amount between the spectra signals obtained for the azimuth angles;
if the difference amount is above a predetermined threshold, determining and reporting that the particular structure does not contain a defect; and
if the difference amount is equal to or lower than the predetermined threshold or equal to zero, determining and reporting that the particular structure contains a defect, wherein such defect is below a surface of the particular structure.

15. The system of claim 14, wherein determining that the particular structure contains or does not contain a defect is performed without use of a model or extraction of a quantitative feature value from such particular structure.

16. The system of claim 14, wherein the difference amount is an average difference of a plurality of differences between the spectra signals at the azimuth angles over a plurality of wavelengths.

17. The system of claim 16, the processor and memory being configured for:
determining theoretical or measured difference amounts between spectra signals for the azimuth angles for a nondefective grating structure; and
normalizing the average difference by the theoretical or measured difference amounts to determine a defect quantity.

18. The system of claim 14, wherein the difference amount is a highest one of a plurality of differences between the spectra signals at the azimuth angles at a particular one of a plurality of wavelength ranges.

19. The system of claim 14, wherein measuring spectra includes generating a differential model by using two dimensional beam profile reflectometry.

20. The system of claim 19, the processor and memory being configured for determining a difference between the differential model between an image and best fit of a radially symmetric image.

21. The system of claim 14, wherein the particular structure is selected from a Directed Self Assembly (DSA) structure, under layer non-Directed Self Assembly (non-DSA) structure, or patterned resist structure.

22. The system of claim 14, the processor and memory being configured for:
collecting reference data that quantifies pattern defects using a CD SEM tool;
obtaining spectra signals at the azimuth angles from a training set of pattern structures having known pattern defects;
determining a first relation function between spectra signals measured at different azimuth angles and a residual error, wherein the first relationship is based on the spectra signals obtained at the azimuth angles from the training set;
determining a second relation function between a residual error and a quantification of pattern defects based on the reference data; and
inputting the spectra signals measured from the particular structure at the azimuth angles into the second relation function to determine a quantification of pattern defects for such particular structure.

23. The system of claim 22, wherein the first and second relation functions are based on a data reduction technique applied to the spectra signals and residual errors for the training set and the particular structure.

24. The system of claim 14, wherein the defect is a subsurface defect.

25. The system of claim 24, wherein the particular structure is a Directed Self Assembly (DSA) structure, wherein correcting the particular structure and/or correcting the manufacturing process comprises correcting a chemoepitaxy of the DSA structure.

26. The system of claim 24, wherein the particular structure is a Directed Self Assembly (DSA) structure, wherein correcting the particular structure and/or correcting the manufacturing process comprises correcting a photolithography process' exposure and/or dose for forming the DSA structure.

27. A method of characterizing a film of interest on a semiconductor wafer, the method comprising:
at one or more sensors of a metrology system, measuring a plurality of spectra signals from a plurality of neighboring locations at a measurement site of the film or a structure that is designed to be uniform across the measurement site;
determining an average or mean signal of the spectra signals;
determining a standard deviation of each of the spectra signals at each location from the average or mean signal;
if one or more of the standard deviations of the spectra signals is above a predetermined threshold from the average or mean, determining and reporting that the film or structure contains a defect; and
if one or more of the standard deviations of the spectra signals is equal to or lower than the predetermined threshold or equal to zero, determining and reporting that the film or structure does not contain a defect.

* * * * *